(12) United States Patent
Schmid et al.

(10) Patent No.: US 7,605,263 B2
(45) Date of Patent: Oct. 20, 2009

(54) FLUORESCENT NAPHTHALENE-1,4,5,8-TETRACARBOXYLIC BISIMIDES WITH AN ELECTRON-DONATING SUBSTITUENT ON THE NUCLEUS

(75) Inventors: Gunter Schmid, Hemhofen (DE); Christoph Thalacker, Weilheim (DE); Frank Wurthner, Ulm (DE)

(73) Assignee: Infineon Technologies AG, Munich (DE)

( * ) Notice: Subject to any disclaimer, the term of this patent is extended or adjusted under 35 U.S.C. 154(b) by 161 days.

(21) Appl. No.: 10/254,470

(22) Filed: Sep. 25, 2002

(65) Prior Publication Data

US 2003/0153005 A1 Aug. 14, 2003

(30) Foreign Application Priority Data

Sep. 28, 2001 (DE) .................. 101 48 172

(51) Int. Cl.
*C07D 471/04* (2006.01)
*C07D 221/18* (2006.01)
(52) U.S. Cl. .............. 546/62; 546/66; 546/70
(58) Field of Classification Search ............ 546/62, 546/66, 70
See application file for complete search history.

(56) References Cited

U.S. PATENT DOCUMENTS 2,914,531 A * 11/1959 Steuble et al. ............. 544/212

FOREIGN PATENT DOCUMENTS

| EP | 0 553 950 A2 | 8/1993 |
| EP | 553950 | * 8/1993 |
| GB | 942555 | * 11/1963 |
| GB | 1124536 | 8/1968 |
| GB | 1147232 | 4/1969 |

OTHER PUBLICATIONS

Caplus English Abstract DN 85:48244 Bonnet Evelyn et al 1976 pp. 504-506.*
GB 1147232 Boyd Violet et al 1969.*
GB 942555, Badiche Aniline et 1963.*
Caplus , English Abstract DN 85:48244 Bonnet Evelyn et al, RN # 59723-32, 1976.*
DN 71:31350 Boyd Violet et al English Abstract GB 1147232 RN# 2206-13-9, 1969.*
English Abstract DN 62 :468 Abstract GB 962555 RN # 31392-90. 1962.*
Caplus , English Abstract JP 02255789, Mori 1990.*
Wikepedia definition of fluoresence ,2007.*
Wikepedia definition of dyes 2007.*
Bondarenko et al., "Derivatives of naphthalene-1,4,5,8-tetracarboxylic acid. III. Aminolysis of bisimides of naphthalene-1,4,5,8-tetracarboxylic acid and its substituted derivatives", Online, p. 2377-82, (1983).

* cited by examiner

*Primary Examiner*—Rita J Desai
(74) *Attorney, Agent, or Firm*—Patterson & Sheridan, L.L.P.

(57) ABSTRACT

Naphthalene-1,4,5,8-tetracarboxylic bisimides of the general formula I

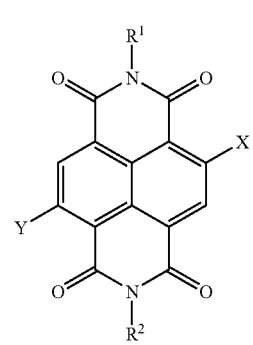

where the variables are defined as follows:
$R^1$ and $R^2$ independently of one another are hydrogen, substituted or unsubstituted alkyl or substituted or unsubstituted aryl;
X and Y independently of one another are halogen, amino or a radical with the formula $-NHR^3$, $-OR^3$, where $R^3$ has the formula $-CH_2R^4$, $-CHR^4R^5$, or $-CR^4R^5R^6$, where $R^4$, $R^5$, and $R^6$ independently of one another are hydrogen, substituted or unsubstituted alkyl, aryl, alkoxy, alkylthio, aryloxy or arylthio, and at least one of the two substituents X and Y is other than halogen,
their preparation and use as fluorescent dyes, for coloring high molecular mass organic materials and inorganic materials, as laser dyes, and also for fluorescence marking and as fluorescent labels for biomolecules.

15 Claims, No Drawings

US 7,605,263 B2

FLUORESCENT NAPHTHALENE-1,4,5,8-TETRACARBOXYLIC BISIMIDES WITH AN ELECTRON-DONATING SUBSTITUENT ON THE NUCLEUS

TECHNICAL FIELD

The present invention relates to novel naphthalene-1,4,5,8-tetracarboxylic bisimides (referred to below for short as naphthalene bisimides) of the general formula I

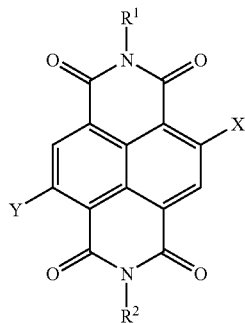

where the variables are defined as follows:

$R^1$ and $R^2$ independently of one another are hydrogen, substituted or unsubstituted alkyl or substituted or unsubstituted aryl;

X and Y independently of one another are halogen, amino or a radical with the formula —$NHR^3$, —$OR^3$, where $R^3$ has the formula —$CH_2R^4$, —$CHR^4R^5$, or —$CR^4R^5R^6$, where $R^4$, $R^5$, and $R^6$ independently of one another are hydrogen, substituted or unsubstituted alkyl, aryl, alkoxy, alkylthio, aryloxy or arylthio, and at least one of these two substituents X and Y is other than halogen, and with the exception of the following compound:

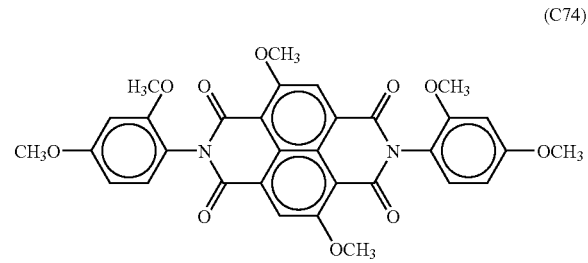

(C74)

The invention further relates to the preparation of these naphthalene bisimides and to their use for applications as fluorescent dyes, as laser dyes, for fluorescence marking or as fluorescent labels for biomolecules, the compound mentioned above not being excepted in relation to said use.

BACKGROUND ART

The following nuclear-substituted naphthalene bisimide dyes have been disclosed to date:

Liebigs Ann. 531, pp. 1–159 (1937), Zh. Org. Khim. 15, pp. 2520–2525 (1979), and Zh. Org. Khim. 18, pp. 610–615 (1982) describe naphthalene bisimides which are functionalized on the naphthalene nucleus by halogen and arylamino substituents. These compounds, however, do not exhibit any fluorescence.

EP 0 553 950 A2 discloses a nuclear-substituted naphthalene bisimide compound having two —$OCH_3$ groups on the naphthalene nucleus. Fluorescence of the compound is not described. GB 1,147,232 and GB 1,124,536 describe naphthalene bisimides which do not fluoresce and which have an aminoaryl group on the naphthalene nucleus. E. F. Bondarenko et al., "Derivatives of naphthalene-1,4,5,8-tetracarboxylic acid. Aminolysis of bisimides of naphthalene-1,4,5,8-tetracarboxylic acid and its substituted derivatives", Zh. Org. Khim. 1983, 19(11), 2377–82, HCAPLUS, Accession No. 1984:209748, disclose various naphthalene bisimides with single substitution on the naphthalene nucleus. No fluorescence is described.

SUMMARY OF THE INVENTION

The invention was based on the object of providing fluorescent naphthalene bisimides whose optical properties can be adjusted over a wide range by the targeted introduction of suitable substituents on the naphthalene nucleus.

Accordingly, the naphthalene bisimides of the formula I defined at the outset have been found. These dyes surprisingly exhibit an intense fluorescence in organic and aqueous solvents, and in addition encompass all desirable shades from blue via green and yellow through to red as a function of the respective nuclear substituents.

Preferred naphthalene bisimides of the formula I are evident from the following description and from the subclaims.

The present invention further relates to a process for preparing these naphthalene bisimides, which is characterized in that a naphthalene bisimide of the general formula IIa or IIb

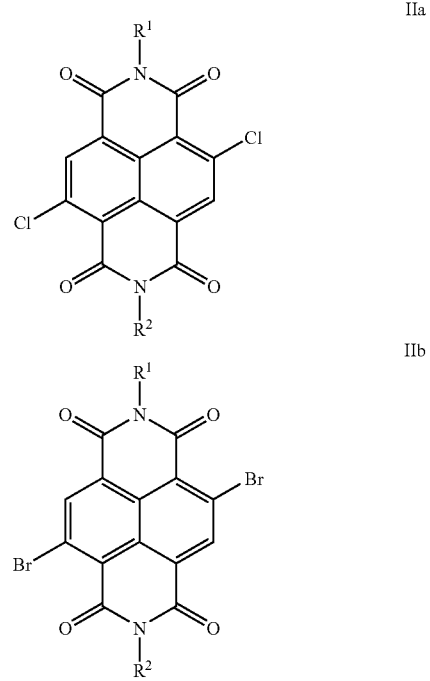

is reacted with nucleophiles of the formula H—X and/or H—Y in an organic solvent, it being possible for H—X and/or H—Y to take on the function of the solvent as well, and where X and Y are as defined above.

DETAILED DESCRIPTION OF THE INVENTION

Found not least has been the use of the naphthalene bisimides of the formula I for applications for coloring high molecular mass organic materials and inorganic materials, as fluorescent dyes, as laser dyes, for fluorescence marking and/or as fluorescent labels for biomolecules. For these uses, the compound (C74) is not excepted in accordance with the invention. In one preferred embodiment, however, the compound (C74) is excepted from said use.

The variables in formula I will be elucidated further below. Examples of suitable nonhydrogen radicals $R^1$ and $R^2$ are:

$C_1$-$C_{30}$ alkyl whose carbon chain may be interrupted by one or more groups —O—, —S—, —$NR^7$—, —CO— and/or —$SO_2$— and which may be substituted one or more times by carboxyl, sulfo, hydroxyl, cyano, $C_1$–$C_6$ alkoxy or a 5- to 7-membered heterocyclic radical which is attached by a nitrogen atom, which may contain further heteroatoms, and which may be aromatic, $R^7$ being hydrogen or $C_1$–$C_6$ alkyl;

$C_5$–$C_8$ cycloalkyl whose carbon framework may be interrupted by one or more groups —O—, —S— and/or —$NR^3$—, $R^3$ being as defined above;

phenyl which is substituted one or more times by $C_1$–$C_4$ alkyl or methoxy, preferably in both ortho positions and/or by $C_5$–$C_{18}$ alkyl, $C_2$–$C_6$ alkoxy, halogen, hydroxyl, cyano, carboxyl, —$CONHR^8$, —$NHCOR^8$ and/or arylazo or hetarylazo, each of which may be substituted by $C_1$–$C_{10}$ alkyl, $C_1$–$C_6$ alkoxy, halogen, hydroxyl, cyano or carboxyl, $R^8$ being hydrogen; $C_1$–$C_{18}$ alkyl; or aryl or hetaryl, each of which may be substituted by $C_1$–$C_6$ alkyl, $C_1$–$C_6$ alkoxy, halogen, hydroxyl or cyano;

naphthyl or hetaryl each of which may be substituted by the substituents stated for phenyl, it being possible for the $C_1$–$C_4$ alkyl substituents and methoxy to occupy any desired positions on the ring system.

All of the alkyl groups occurring in the abovementioned formulae may be both straight-chain and branched.

Specific examples of preferred substituents $R^1$ and/or $R^2$, which are also preferred radicals for $R^3$, $R^4$, $R^5$ and/or $R^6$, are:

methyl, ethyl, propyl, isopropyl, butyl, isobutyl, tert-butyl, pentyl, isopentyl, neopentyl, tert-pentyl, hexyl, 2-methylpentyl, tert-pentyl, hexyl, 2-methyl-pentyl, heptyl, 1-ethylpentyl, octyl, 2-ethylhexyl, isooctyl, tert-octyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above designations isooctyl, isononyl, isodecyl and isotridecyl are trivial names and originate from the alcohols obtained in the oxo synthesis), with $C_1$–$C_8$ alkyl radicals and especially tert-butyl being preferred;

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetra-oxatridecyl, and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 4,7-dithiaoctyl, 4,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-mono-isopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazaundecyl, 12-methyl-3,6,9,12-tetraazatridecyl, and 3,6,9,12-tetramethyl-3,6,9,12-tetraazatridecyl;

propan-2-on-1-yl, butan-3-on-1-yl, butan-3-on-2-yl, and 2-ethylpentan-3-on-1-yl; 2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl, and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

methylcarboxymethyl, ethylcarboxymethyl, propylcarboxymethyl-methyl, butylcarboxymethyl, pentylcarboxymethyl, hexylcarboxymethyl, methyl-2-carboxyethyl, ethyl-2-carboxyethyl, propyl-2-carboxyethyl, butyl-2-carboxyethyl, pentyl-2-carboxyethyl, hexyl-2-carboxyethyl, methyl-3-carboxypropyl, ethyl-3-carboxypropyl, propyl-3-carboxypropyl, butyl-3-carboxypropyl, pentyl-3-carboxypropyl, hexyl-3-carboxypropyl, methyl-4-carboxybutyl, methyl-5-carboxypentyl, methyl-6-carboxyhexyl, methyl-8-carboxyoctyl, methyl-10-carboxydecyl, methyl-12-carboxydodecyl, and methyl-14-carboxytetradecyl, 2,3-dicarboxypropyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl, and 14-sulfotetradecyl;

methylsulfomethyl, ethylsulfomethyl, propylsulfomethyl, butylsulfomethyl, pentylsulfomethyl, hexylsulfomethyl, methyl-2-sulfoethyl, ethyl-2-sulfoethyl, propyl-2-sulfoethyl, butyl-2-sulfoethyl, pentyl-2-sulfoethyl, hexyl-2-sulfoethyl, methyl-3-sulfopropyl, ethyl-3-sulfopropyl, propyl-3-sulfopropyl, butyl-3-sulfopropyl, pentyl-3-sulfopropyl, hexyl-3-sulfopropyl, methyl-4-sulfobutyl, methyl-5-sulfopentyl, methyl-6-sulfohexyl, methyl-8-sulfooctyl, methyl-10-sulfodecyl, methyl-12-sulfododecyl, and methyl-14-sulfotetradecyl;

2-hydroxyethyl, 2- and 3-hydroxypropyl, 1-hydroxyprop-2-yl, 2- and 4-hydroxybutyl, 1-hydroxybut-2-yl, and 8-hydroxy-4-oxaoctyl, 5-hydroxy-3-oxapentyl, 6-hydroxy-3-oxahexyl, 8-hydroxy-3,6-dioxaoctyl, and 11-hydroxy-3,6,9-trioxaundecyl;

2-aminoethyl, 2- and 3-aminopropyl, 1-aminoprop-2-yl, 2- and 4-aminobutyl, 1-aminobut-2-yl, and 8-amino-4-oxaoctyl, 5-amino-3-oxapentyl, 6-amino-3-oxahexyl, 8-amino-3,6-dioxaoctyl, and 11-amino-3,6,9-trioxaundecyl;

2-methylaminoethyl, 2- and 3-methylaminopropyl, 1-methylaminoprop-2-yl, 2- and 4-methylaminobutyl, 1-methylaminobut-2-yl, and 8-methylamino-4-oxaoctyl, 5-methylamino-3-oxapentyl, 6-methylamino-3-oxahexyl, 8-methylamino-3,6-dioxaoctyl, and 11-methylamino-3,6,9-trioxaundecyl;

2-dimethylaminoethyl, 2- and 3-dimethylaminopropyl, 1-dimethylaminoprop-2-yl, 2- and 4-dimethylaminobutyl, 1-dimethylaminobut-2-yl, and 8-dimethylamino-4-oxaoctyl, 5-dimethylamino-3-oxapentyl, 6-dimethylamino-3-oxahexyl, 8-dimethylamino-3,6-dioxaoctyl, and 11-dimethylamino-3,6,9-trioxaundecyl;

2-cycanoethyl, 3-cyanopropyl, 2-methyl-3-ethyl-3-cyanopropoyl, 7-cyano-7-ethylheptyl, and 4-methyl-7-methyl-7-cyanoheptyl;

cyclopentyl, cyclohexyl, cycloheptyl, cyclooctyl, 2-dioxanyl, 4-morpholinyl, 2- and 3-tetrahydrofuryl, 1-, 2- and 3-pyrrolidinyl, and 1-, 2-, 3-, and 4-piperidyl.

Further suitable substituents $R^1$, $R^2$, $R^4$, $R^5$, and $R^6$ include:

phenyl, 2-naphthyl, 2- and 3-pyrryl, 2-, 3-, and 4-pyridyl, 2-, 4-, and 5-pyrimidyl, 3-, 4-, and 5-pyrazolyl, 2-, 4-, and 5-imidazolyl, 2-, 4-, and 5-thiazolyl, 3-(1,2,4-triazyl), 2-(1,3,5-triazyl), 6-quinaldyl, 3-, 5-, 6-, and 8-quinolyl, 2-benzoxazolyl, 2-benzothiazolyl, 2- and 5-benzimidazolyl, and 1- and 5-isoquinolyl;

2-, 3-, and 4-methylphenyl, 2,4-, 3,5- and 2,6-dimethylphenyl, 2,4,6-trimethylphenyl, 2-, 3-, and 4-ethylphenyl, 2,4-, 3,5-, and 2,6-diethylphenyl, 2,4,6-triethylphenyl, 2-, 3-, and 4-propylphenyl, 2,4-, 3,5-, and 2,6-dipropylphenyl, 2,4,6-tripropylphenyl, 2-, 3-, and 4-isopropylphenyl, 2,4-, 3,5-, and 2,6-diisopropylphenyl, 2,4,6-triisopropylphenyl, 2-, 3-, and 4-butylphenyl, 2,4-, 3,5-, and 2,6-dibutylphenyl, 2,4,6-tributylphenyl, 2-, 3-, and 4-isobutylphenyl, 2,4-, 3,5-, and 2,6-diisobutylphenyl, 2,4,6-triisobutylphenyl, 2-, 3-, and 4-sec-butylphenyl, 2,4-, 3,5-, and 2,6-di-sec-butylphenyl, 2,4,6-tri-sec-butylphenyl, 2-, 3-, and 4-methoxyphenyl, 2,4-, 3,5-, and 2,6-dimethoxyphenyl, 2,4,6-trimethoxyphenyl, 2-, 3-, and 4-ethoxyphenyl, 2,4-, 3,5-, and 2,6-diethoxyphenyl, 2,4,6-triethoxyphenyl, 2-, 3-, and 4-propoxyphenyl, 2,4-, 3,5-, and 2,6-dipropoxyphenyl, 2,4,6-tripropoxyphenyl, 2-, 3-, and 4-isopropoxyphenyl, 2,4-, 3,5-, and 2,6-diisopropoxyphenyl, 2-, 3-, and 4-butoxyphenyl; 2-, 3-, and 4-chlorophenyl, 2,4-, 3,5-, and 2,6-dichlorophenyl; 2-, 3-, and 4-hydroxyphenyl, 2,4-, 3,5-, and 2,6-dihydroxyphenyl; 2-, 3-, and 4-cyanophenyl; 3- and 4-carboxyphenyl; 3- and 4-carboxyamidophenyl; 3- and 4-N-methylcarboxamidophenyl, and 3- and 4-N-ethylcarboxamidophenyl; 3- and 4-acetylaminophenyl, 3- and 4-propionylaminophenyl, and 3- and 4-butyrylaminophenyl; 3- and 4-N-phenylaminophenyl, 3- and 4-N-(o-tolyl)aminophenyl, 3- and 4-N-(m-tolyl)aminophenyl, and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl, and 4-(4-pyrimidyl)-aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl, and 4-(5-pyrimidylazo)phenyl.

Particularly preferred radicals for $R^1$ and/or $R^2$ are, independently of one another, hydrogen, $C_1$–$C_{20}$ alkyl, more preferably $C_1$–$C_8$ alkyl, especially tert-butyl, or phenyl, which may be singly substituted by $C_1$–$C_8$ alkyl.

Suitable radicals for $R^7$ are: methyl, ethyl, propyl, isopropyl, butyl, isobutyl, tert-butyl, pentyl, isopentyl, neopentyl, tert-pentyl, hexyl, 2-methylpentyl, tert-pentyl, hexyl, and 2-methylpentyl.

X and/or Y are preferably, independently of one another, hydrogen, halogen, $C_1$–$C_{20}$ alkylamino or $C_1$–$C_{20}$ alkoxy, it being possible for the carbon chain of $C_1$–$C_{20}$ alkoxy and of $C_1$–$C_{20}$ alkylamino to be interrupted in each case by up to four ether bridges and also to carry hydroxyl, carboxyl, amino, alkylamino, dialkylamino or sulfonic acid groups at the end, at least one of the substituents X and Y being other than hydrogen and halogen.

Examples of particularly preferred substituents x and/or Y on the naphthalene nucleus, independently of one another and with at least one of the substituents X and Y being other than halogen, are: chlorine, bromine, propylamino, isopropylamino, butylamino, sec-butylamino, tert-butylamino, pentylamino, isopentylamino, neopentylamino, tert-pentylamino, hexylamino, 2-methylpentylamino, heptylamino, octylamino, 2-ethylhexylamino, isooctylamino, nonylamino, isononylamino, decylamino, isodecylamino, undecylamino, dodecylamino, tridecylamino, tetradecylamino, pentadecylamino, hexadecylamino, heptadecylamino, octadecylamino, nonadecylamino, eicosylamino, 2-hydroxyethylamino, 2- and 3-hydroxypropylamino, 1-hydroxyprop-2-yl-amino, 2- and 4-hydroxybutylamino, 1-hydroxybut-2-yl-amino, and 8-hydroxy-4-oxooctylamino, 5-hydroxy-3-oxapentylamino, 6-hydroxy-3-oxahexylamino, 8-hydroxy-3,6-dioxaoctylamino, 11-hydroxy-3,6,9-undecylamino; 2-methoxyethylamino, 2-ethoxyethylamino, 2-propoxyethylamino, 2-isopropoxyethylamino, 2-butoxyethylamino, 2- and 3-methoxypropylamino, 2- and 3-ethoxypropylamino, 2- and 3-propoxypropylamino, 2- and 3-butoxypropylamino, 2- and 4-methoxybutylamino, 2- and 4-ethoxybutylamino, 2- and 4-propoxybutylamino, 3,6-dioxaheptylamino, 3,6-dioxaoctylamino, 4,8-dioxanonylamino, 3,7-dioxaoctylamino, 3,7-dioxanonylamino, 4,7-dioxaoctylamino, 4,7-dioxanonylamino, 2- and 4-butoxybutylamino, 4,8-dioxadecylamino, 3,6,9-trioxadecylamino, 3,6,9-trioxaundecylamino, 3,6,9-trioxadodecylamino, 3,6,9,12-tetraoxatridecylamino, and 3,6,9,12-tetraoxatetradecylamino;

ethoxy, propoxy, isopropoxy, butoxy, sec-butoxy, tert-butoxy, pentyloxy, isopentyloxy, neopentyloxy, tert-pentyloxy, hexyloxy, 2-methylpentyloxy, heptyloxy, octyloxy, 2-ethylhexyloxy, isooctyloxy, nonyloxy, isononyloxy, decyloxy, isodecyloxy, undecyloxy, dodecyloxy, tridecyloxy, tetradecyloxy, pentadecyloxy, hexadecyloxy, heptadecyloxy, octadecyloxy, nonadecyloxy, eicosyloxy, 2-hydroxyethyloxy, 2- and 3-hydroxypropyloxy, 1-hydroxyprop-2-yloxy, 2- and 4-hydroxybutoxy, 1-hydroxybut-2-yloxy, and 8-hydroxy-4-oxaoctyloxy, 5-hydroxy-3-oxapentyloxy, 6-hydroxy-3-oxahexyloxy, 8-hydroxy-3,6-dioxaoctyloxy, 11-hydroxy-3,6,9-undecyloxy; 2-methoxyethoxy, 2-ethoxyethoxy, 2-propoxyethoxy, 2-isopropoxyethoxy, 2-butoxyethoxy, 2- and 3-methoxypropoxy, 2- and 3-ethoxypropoxy, 2- and 3-propoxypropoxy, 2- and 3-butoxypropoxy, 2- and 4-methoxybutoxy, 2- and 4-ethoxybutoxy, 2- and 4-propoxybutoxy, 3,6-dioxaheptyloxy, 3,6-dioxaoctyloxy, 4,8-dioxanonyloxy, 3,7-dioxaoctyloxy, 3,7-dioxanonyloxy, 4,7-dioxaoctyloxy, 4,7-dioxanonyloxy, 2- and 4-butoxybutoxy, 4,8-dioxadecyloxy, 3,6,9-trioxadecyloxy, 3,6,9-trioxaundecyloxy, 3,6,9-trioxadodecyloxy, 3,6,9,12-tetraoxatridecyloxy, and 3,6,9,12-tetraoxatetradecyloxy.

The naphthalene bisimides of the formula I according to the invention may advantageously be prepared by the process which is likewise in accordance with the invention and in which the substituted naphthalene-1,4,5,8-tetracarboxylic bisimides of the formula IIa and/or IIb are reacted with identical nucleophiles H—X or H—Y or with different nucleophiles H—X and H—Y in an organic solvent. In this case, H—X and/or H—Y may also take on the function of the solvent.

Suitable nucleophiles, in accordance with the invention, are alkylamines, alkoxyamines, amino alcohols, alcohols, alkali metal alkoxides, thiols, and thiolates.

Examples of particularly preferred nucleophiles H—X are propylamine, isopropylamine, butylamine, sec-butylamine, tert-butylamine, pentylamine, isopentylamine, neopentylamine, tert-pentylamine, hexylamine, 2-methylpentylamine, heptylamine, octylamine, 2-ethylhexylamine, isooctylamine, nonylamine, isononylamine, decylamine, isodecylamine, undecylamine, dodecylamine, tridecylamine, tetradecylamine, pentadecylamine, hexadecylamine, heptadecylamine, octadecylamine, nonadecylamine and eicosylamine, 2-hydroxyethylamine, 2- and 3-hydroxypropylamine, 1-hydroxyprop-2-ylamine, 2- and 4-hydroxybutylamine, 1-hydroxybut-2-ylamine and 8-hydroxy-4-oxaoctylamine, 5-hydroxy-3-oxapentylamine, 6-hydroxy-3-oxahexylamine, 8-hydroxy-3,6-dioxaoctylamine, 11-hydroxy-3,6,9-undecylamine; 2-methoxyethylamine, 2-ethoxyethylamine, 2-propoxyethylamine, 2-isopropoxyethylamine, 2-butoxyethylamine, 2- and 3-methoxypropylamine, 2- and 3-ethoxypropylamine, 2- and 3-propoxypropylamine, 2- and 3-butoxypropylamine, 2- and 4-methoxybutylamine, 2- and 4-ethoxybutylamine, 2- and 4-propoxybutylamine, 3,6-dioxaheptylamine, 3,6-dioxaoctylamine, 4,8-dioxanonylmaine, 3,7-dioxaoctylamine, 3,7-dioxanonylamine, 4,7-dioxaoctylamine, 4,7-dioxanonylamine, 2- and 4-butoxybutylamine, 4,8-dioxadecylamine, 3,6,9-trioxadecylamine, 3,6,9-trioxaundecylamine, 3,6,9-trioxadodecylamine, 3,6,9,12-tetraoxatridecylamine, and 3,6,9,12-tetraoxatetradecylamine.

The substituent $OR^3$ may be introduced even at room temperature, owing to the heightened reactivity, by reacting the bishalo compounds with the corresponding alkoxides.

Particularly suitable organic solvents here are halogenated solvents such as dichloromethane, chloroform, and chlorobenzene and/or polar aprotic solvents such as N-methylpyrrolidone, dimethylformamide, and quinoline, and also alcohols, with particular preference being given to dichloromethane and chlorobenzene.

The amount of solvent is not critical per se. It is possible with preference to use from 5 to 120 g of solvent per g of naphthalene-1,4,5,8-tetracarboxylic bisimide (IIa or IIb).

The molar ratio of nucleophile H—X to the naphthalene-1,4,5,8-tetracarboxylic bisimide (IIa or IIb) is normally from about 2:1 to 10:1, preferably from about 2:1 to 5:1.

The reaction temperature is generally from 20 to 200° C., preferably 20–50° C. for the introduction of a radical X and/or Y and 100–200° C. for the introduction of two radicals X and/or Y, with particular preference 20–30° C. for the introduction of a radical X and/or Y and 130–150° C. for the introduction of two radicals X and/or Y.

It is preferred to conduct the reaction under an inert gas atmosphere, preferably argon or else nitrogen.

In general it is unnecessary to operate under pressure in the case of this process according to the invention.

The reaction is normally over after from 1 to 4 h.

An appropriate procedure is as follows:

2,6-dichloronaphthalene-1,4,5,8-tetracarboxylic bisimide (IIa) or 2,6-dibromonaphthalene-1,4,5,8-tetracarboxylic bisimide (IIb) and solvent are introduced as initial charge, the nucleophile H—X is added with stirring at room temperature, the apparatus is flushed with argon for about 10 minutes, and the mixture is heated to the reaction temperature with stirring and is held at said temperature for about 1 to 5 hours. After cooling to room temperature, the reaction mixture is introduced into approximately three times the volume of the dilute inorganic acid, e.g., from 5 to 10% strength by weight hydrochloric acid, and the precipitated reaction product is filtered off, washed first with water until the runoff is neutral and then with an aliphatic alcohol such as methanol, and dried in vacuo.

For subsequent purification the product may be recrystallized (for example, from an aliphatic alcohol such as isopropanol) or subjected to column chromatography (e.g., silica gel/dichloromethane).

Where the 2,6-dichloronaphthalene-1,4,5,8-tetracarboxylic bisimide (IIa) is to be reacted with two different nucleophiles, the reaction is appropriately performed in stages, by first introducing one nucleophile, H—X or H—Y, at a temperature of from 20 to 30° C. and, following isolation of the intermediate in the manner described above, introducing the other nucleophile, H—Y and/or H—X, at a temperature of from 130 to 150° C.

With the aid of the process of the invention it is possible to obtain the naphthalene bisimides of the formula I advantageously in high purity (purity generally ≧95% strength) and good yield (generally from 70 to 98%).

The 2,6-dichloronaphthalene-1,4,5,8-tetracarboxylic bisimides (IIa) which serve as starting materials for this preparation process according to the invention are known per se or can be prepared by known methods starting from 2,6-dichloronaphthalene-1,4,5,8-tetracarboxylic bisanhydride (cf. Liebigs Ann. 531, pp. 1–159 (1937)).

The 2,6-dibromonaphthalene-1,4,5,8-tetracarboxylic bisimides (IIb) which serve as starting materials for this preparation process according to the invention can be prepared by known methods starting from 2,6-dibromonaphthalene-1,4,5,8-tetracarboxylic bisanhydride (cf. Liebigs Ann. 531, pp. 1–159 (1937)). 2,6-Dibromonaphthalene-1,4,5,8-tetracarboxylic bisanhydride can be obtained by brominating the 1,4,5,8-tetracarboxylic bisanhydride with strong brominating reagents such as dibromoisocyanuric acid in oleum, for example.

On account of their intense fluorescence, the naphthalene bisimides of the formula I according to the invention are outstandingly suitable for a host of applications, particularly as fluorescent colorants for coloring high molecular mass organic materials (e.g. polyolefins) and inorganic materials. They may further find application as laser dyes, for fluorescence marking, or, not least, may be used as fluorescent labels for biomolecules.

The invention is described below with reference to examples which are not, however, intended to restrict the scope of the invention.

EXAMPLES

A) Preparation of Inventive Naphthalene Bisimides

Example 1

N,N'-Di-n-octyl-2-chloro-6-n-octylaminonaphthalene-1,4,5,8-tetracarboxylic Bisimide:

A mixture of 0.16 g (0.28 mmol) of N,N'-di-n-octyl-2,6-dichloronaphthalene-1,4,5,8-tetracarboxylic bisimide, 1 ml (6.0 mmol) of n-octylamine and 20 ml of dichloromethane was stirred at room temperature for 4.5 hours.

The reaction mixture was subsequently poured with stirring into a mixture of 2 ml of 36% strength by weight hydrochloric acid and 70 ml of methanol. This mixture was concentrated in vacuo at room temperature. The red precipitate obtained was filtered off with suction, washed with water and with methanol, and dried at room temperature under a medium high vacuum.

This gave 0.18 g of product having a purity of 99%, corresponding to a yield of 96%.

Analytical Data:

Elemental analysis for $C_{38}H_{54}ClN_3O_4$ (652.3) (% by weight calc./found):

C: 69.97/69.70; H: 8.34/8.36; N: 6.44/6.44;

1H-NMR (400 MHz, CDCl$_3$, 25° C., TMS): δ=10.05 (t, $^3$J(H,H)=5.2 Hz, 1 H, NH), 8.60 (s, 1 H, H3), 8.26 (s, 1 H, H7), 4.15 (m, 4 H, NC$\underline{H}_2$), 3.57 (m, 2 H, NHC$\underline{H}_2$), 1.83 (m, 2H, NHCH$_2$C$\underline{H}_2$), 1.72 (m, 4 H, NCH$_2$C$\underline{H}_2$), 1.5–1.2 (m, 30 H), 0.89 (m, 9 H, CH$_3$) ppm;

UV/Vis (CH$_2$Cl$_2$): $\lambda_{max}$(ε)=532 (15 300), 504 (11 400, sh), 367 (13 100), 348 (10 700), 331 (8 300, sh), 271 nm (43 100 mol$^{-1}$ dm$^3$ cm$^{-1}$)

Example 2

N,N'-Di-n-octyl-2,6-di-n-octylaminonaphthalene-1,4,5,8-tetracarboxylic bisimide

A mixture of 0.37 g (0.67 mmol) of N,N'-di-n-octyl-2,6-dichloronaphthalene-1,4,5,8-tetracarboxylic bisimide and 3 ml of n-octylamine was heated at 140° C. under argon for 40 minutes.

After cooling to room temperature, the reaction mixture was poured with stirring into a mixture of 3 ml of 36% strength by weight hydrochloric acid and 50 ml of methanol. The resultant blue precipitate was filtered off with suction, purified by recrystallization from isopropanol, and dried at 50° C. under a medium high vacuum.

This gave 0.35 g of product having a purity of 99%, corresponding to a yield of 70%.

Analytical Data:

Elemental analysis for $C_{46}H_{72}N_4O_4$ (745.1) (% by weight calc./found):

C: 74.15/73.92; H: 9.74/9.61; N: 7.52/7.50;

1H-NMR (400 MHz, CDCl$_3$, 25° C., TMS): δ=9.33 (t, $^3$J(H,H)=5.1 Hz, 2 H, N$\underline{H}$CH$_2$), 8.13 (s, 2 H, H3, 7), 4.16 (t, $^3$J(H,H)=7.8 Hz, 4 H, NC$\underline{H}_2$), 3.48 (m, 4 H, NHC$\underline{H}_2$), 1.80 (m, 4 H, NHCH$_2$C$\underline{H}_2$), 1.72 (m, 4 H, NCH$_2$C$\underline{H}_2$), 1.5–1.2 (m, 40 H), 0.88 (m, 12 H, CH$_3$) ppm;

UV/Vis (CH$_2$Cl$_2$): $\lambda_{max}$(ε)=615 (23 000), 575 (12 600, sh), 364 (13 600), 346 (10 800), 331 (6 300, sh), 282 nm (46 800 mol$^{-1}$ dm$^3$ cm$^{-1}$).

Example 3

N,N'-Di-(4-tert-butylphenyl)-2-chloro-6-noctylaminonaphthalene-1,4,5,8-tetracarboxylic bisimide In analogy to example 1, starting from 30 mg (0.05 mmol) of N,N'-di-(4-tert-butylphenyl)-2,6-dichloronaphthalene-1,4,5,8-tetracarboxylic bisimide and 0.12 ml (0.72 mmol) of n-octylamine in 4 ml of dichloromethane, column chromatography (dichloromethane: hexane =2:1, silica gel) gave 30 mg of N,N'-di-(4-tert-butylphenyl)-2-chloro-6-n-octylaminonaphthalene-1,4,5,8-tetracarboxylic bisimide having a purity of 99%, corresponding to a yield of 87%.

Analytical Data:

Elemental analysis for $C_{42}H_{46}ClN_3O_4$ (692.3) (% by weight calc./found):

C: 72.87/72.91; H: 6.70/6.52; N: 6.07/6.12;

UV/Vis (CH$_2$Cl$_2$): $\lambda_{max}$(ε)=534 (16 000), 505 (11 800, sh), 365 (14 400), 348 (13 300), 332 (9 200, sh), 270 nm (39 500 mol$^{-1}$ dm$^3$ cm$^{-1}$)

Example 4

N,N'-Di(2-ethylhexyl)-2,6-di(2-ethylhexylamino)-naphthalene-1,4,5,8-tetracarboxylic bisimide 2.12 g (5.0 mmol) of 2,6-dibromonaphthalene-1,4,5,8-tetracarboxylic anhydride are heated in 15 ml of 2-ethylhexylamine under reflux at 140° C. in an argon atmosphere for two hours. A dark blue solution is formed which after cooling is poured into a mixture of 10 ml of concentrated HCl (hydrochloric acid) and 100 ml of methanol. The resultant blue precipitate is filtered off and washed with methanol. Purification by column chromatography on silica gel (eluent: dichloromethane:hexane=2:1) gave 1.67 g of product having a purity of 99%, corresponding to a yield of 45%.

Analytical Data:

Elemental analysis for $C_{46}H_{72}N_4O_4$ (745.1) (% by weight calc./found):

C: 74.15/74.12; H: 9.74/9.72; N: 7.52/7.49;

UV/Vis (CH$_2$Cl$_2$): $\lambda_{max}$(ε)=619 (22 100), 576 (11 600, sh), 365 (12 400), 347 (9 700), 330 (4 700, sh), 283 nm (44 800 mol$^{-1}$ dm$^3$ cm$^{-1}$)

B) Properties of Inventive Naphthalene Bisimides

Example 5

Characterizing the Fluorescent Properties of the Naphthalene Bisimide From Example 1:

In dichloromethane, an intense fluorescence was observed with an emission maximum at 567 nm. The fluorescence quantum yield determined for a 5·10$^{-7}$ molar solution was 58%.

Example 6

Characterizing the Fluorescent Properties of the Naphthalene Bisimide From Example 2:

In dichloromethane, an intense fluorescence was observed with an emission maximum at 646 nm. The fluorescence quantum yield determined for a 5·10$^{-7}$ molar solution was 53%.

In analogy to the above examples, the dyes listed in table 1 were prepared by reacting IIa or IIb with nucleophiles and were characterized by UV/Vis absorption spectroscopy and fluorescence spectroscopy. The table lists the absorption maximum $\lambda_{abs}$, the emission maxima $\lambda_{em}$, and the fluorescence quantum yields $\phi_f$.

TABLE 1

| Example No. | R$^1$, R$^2$ | X | Y | UV/Vis $\lambda_{abs}$ | Fluorescence $\lambda_{em}/\phi_f$ |
|---|---|---|---|---|---|
| 7 | 2,6-Diisopropylphenyl | —OEt | —OEt | 469 nm (CH$_2$Cl$_2$) | 483 nm/ 22% (CH$_2$Cl$_2$) |
| 8 | 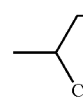 | 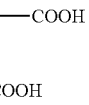 | Cl | 527 nm (ethanol) | 620 nm/ 22% (ethanol) |

TABLE 1-continued

| Example No. | R¹, R² | X | Y | UV/Vis $\lambda_{abs}$ | Fluorescence $\lambda_{em}/\phi_f$ |
|---|---|---|---|---|---|
| 9 | (structure with COOH, COOH, and HO groups) | —NH— (with branched chain) | Cl | 538 nm (water) | 660 nm/ 10% (water) |

Example 10

A $3 \cdot 10^{-7}$ molar solution of the naphthalene bisimide from example 9 in a citrate buffer is suitable for fluorescently labeling apomyoglobin.

Example 11

In a mixture of 80% by weight water and 20% by weight ethanol, a $1.5 \cdot 10^{-7}$ molar solution of the naphthalene bisimide from example 8 was prepared. The same amount of phosphate buffer was then added. Immunoglobulin proteins can be fluorescently labeled using this solution.

Example 12

A red laser printing dye was prepared by subjecting 0.5 g of N,N'-di-n-octyl-2-chloro-6-n-octylamino-naphthalene-1,4,5,8-tetracarboxylic bisimide to very fine trituration in a ball mill (particle size <5 μm) and combining it with a resin base mixture of 8.5 g of styrene-acrylate copolymer (about 70 μm particle size) and 0.3 g of magnetite. The mixture melted at 135° C. to form a dark red spot of color which adheres firmly to paper and overhead films.

Comparative Examples

The following examples, unlike the compounds claimed in this invention where X and/or Y are NHR³, contain aryl substituents on the nitrogen in positions 2 and/or 6 (in other words, X or Y=—NHaryl). These substances are not claimed, since they correspond to the substitution pattern from Liebigs Ann. 531, pp. 1–159 (1937) and GB 1,147,232 and GB 1,124,536. These compounds, however, do not show any fluorescence. Fluorescent dyes are only obtained if a saturated C is attached to the nitrogen, as claimed in accordance with the invention. Evidently, the conjugation which occurs as a result of an unsaturated C (i.e., an aromatic) leads to the extinction of fluorescence.

It was not obvious that the compounds of the invention, in contrast, would show fluorescence.

The following comparative examples show that the known compounds with X or Y=NHaryl do not fluoresce:

Comparative Example 1

N,N'-di-n-octyl-2-chloro-6-(4-tert-butylphenylamino)naphthalene-1,4,5,8-tetracarboxylic bisimide A suspension of N,N'-di-n-octyl-2,6-dichloronaphthalene-1,4,5,8-tetracarboxylic bisimide (0.12 g, 0.2 mmol) and 4-tert-butylaniline (0.1 mL, 0.6 mmol) was stirred in N-ethyldiisopropylamine (3 mL) under argon at 140° C. for 1 h. The red solution obtained was cooled and poured into a mixture of concentrated hydrochloric acid (2 mL) and methanol (10 mL). The precipitated red solid was filtered off and washed with methanol.

This gave 0.14 g of product having a purity of 99%, corresponding to a yield of 97%.

Analytical Data:
Elemental analysis for $C_{40}H_{50}ClN_3O_4$ (672.3): calculated: C, 71.46; H 7.50; N 6.25; found: C, 71.39; H 7.30; N 6.13
Melting point: 113° C.

$^1$H NMR (400 MHz, CDCl$_3$, 25° C., TMS): δ=11.65 (s, 1 H, NH), 8.67 (s, 1 H, H3), 8.56 (s, 1 H, H7), 7.50 (d, $^3$J(H,H)= 6.0 Hz, 2H, $^t$BuPh—H3', 5'), 7.28 (d, $^3$J(H,H)=6.0 Hz, 2 H, $^t$BuPh—H2', 6'), 4.12 (m, 4 H, NCH$_2$), 1.75 (m, 4 H, NCH$_2$CH$_2$), 1.5–1.2 (m, 20 H), 1.38 (s, 9 H, $^t$Bu), 0.87 (m, 6 H, CH$_3$)

UV/Vis (CH$_2$Cl$_2$): $\lambda_{max}$ (ε)=523 (12 900), 369 (11 200), 351 (10 800), 333 (9 000), 286 nm (35 000 mol$^{-1}$ dm$^3$ cm$^{-1}$)

Fluorescence: No fluorescence was detected. The fluorescence quantum yield, taking into account the sensitivity of the apparatus, is therefore <1%.

Comparative Example 2

N,N'-di-n-octyl-2-(4-tert-butylphenylamino)-6-n-octylaminonaphthalene-1,4,5,8-tetracarboxylic bisimide 30 mg (0.045 mmol) of N,N'-di-n-octyl-2,6-dichloronaphthalene-1,4,5,8-tetracarboxylic bisimide from the above example were stirred in n-octylamine (3 mL) under argon at 140° C. for 45 minutes. This produced a blue solution which after cooling was poured into a mixture of concentrated hydrochloric acid (2 mL) and methanol (10 mL). This produced a blue precipitate which was filtered off, washed with methanol, and purified on a silica gel column (eluent: dichloromethane/hexane).

This gave 20 mg of product having a purity of 99%, corresponding to a yield of 59%.

Analytical Data:
Elemental analysis for $C_{48}H_{68}N_4O_4$ (765.1): calculated: C, 75.35; H 8.96; N 7.32; found: C, 75.24; H 9.06; N 7.32.
Melting point: 216° C.

$^1$H NMR (400 MHz, CDCl$_3$, 25° C., TMS): δ=10.95 (s, 1 H, $^t$BuPhNH), 9.52 (t, $^3$J(H,H)=5.2 Hz, 1 H, NHCH$_2$), 8.55 (s, 1 H, H3), 8.17 (s, 1 H, H7), 7.49 (d, $^3$J(H,H)=6.0 Hz, 2 H, $^t$BuPh—H3', 5'), 7.28 (d, $^3$J(H,H)=6.0 Hz, 2 H, $^t$BuPh—H2', 6'), 4.17 (m, 4 H, NCH$_2$), 3.46 (m, 2 H, NHCH$_2$), 1.81 (m, 4 H, NCH$_2$CH$_2$), 1.73 (m, 2 H, NHCH$_2$CH$_2$), 1.5–1.2 (m, 30 H), 1.37 (s, 9 H, $^t$Bu), 0.87 (m, 9 H, CH$_3$);

UV/Vis (CH$_2$Cl$_2$): $\lambda_{max}$ (ε)=613 (22 200), 575 (13 400, sh), 367 (16 000), 349 (13 600), 286 nm (37 900 mol$^{-1}$ dm$^3$ cm$^{-1}$)

Fluorescence: No fluorescence was detected. The fluorescence quantum yield, taking into account the sensitivity of the apparatus, is therefore <1%.

Comparative Example 3

N,N'-di-n-octyl-2,6-di(4-tert-butylphenylamino)naphthalene-1,4,5,8-tetracarboxylic bisimide A suspension of N,N'-di-n-octyl-2,6-dichloronaphthalene-1,4,5,8-tetracarboxylic bisimide (50 mg, 0.09 mmol) in 4-tert-butylaniline (1 mL) is heated under argon at 180° C. for one hour. After cooling the resulting blue solution is poured into a mixture of concentrated hydrochloric acid (2 mL) and ethanol (10 mL) and the blue precipitate produced is filtered off and purified by chromatography on silica gel (eluent: dichloromethane:hexane=2:1). This gave 40 mg of product having a purity of 99.5%, corresponding to a yield of 57%.

Analytical Data:

Elemental analysis for $C_{50}H_{64}N_4O_4$ (785.1): calculated: C, 76.50; H 8.22; N 7.14; found: C, 76.29; H 8.07; N 7.10.

Melting point: 208° C.

$^1$H NMR (400 MHz, CDCl$_3$, 25° C., TMS): δ11.06 (s, 2 H, $^t$BuPhN$\underline{H}$), 8.56 (s, 2 H, H3, 7), 7.50 (d, $^3$J(H,H)=6.0 Hz, 4 H, $^t$BuPh—H3', 5'), 7.28 (d, $^3$J(H,H)=6.0 Hz, $^t$BuPh—H2', 6'), 4.16 (t, 4 H, NC$\underline{H}_2$), 1.72 (m, 4 H, NCH$_2$C$\underline{H}_2$), 1.5-1.2 (m, 20 H), 1.37 (s, 18 H, $^t$Bu), 0.86 (t, $^3$J(H,H)=6.8 Hz, 6 H, CH$_3$)

UV/Vis (CH$_2$Cl$_2$): $\lambda_{max}$ (ε)=612 (22 800), 369 (15 300), 349 (14 800), 311 nm (39 700 mol$^{-1}$ dm$^3$ cm$^{-1}$)

Fluorescence: No fluorescence was detected. The fluorescence quantum yield, taking into account the sensitivity of the apparatus, is therefore <1%.

What is claimed is:

1. A fluorescent naphthalene-1,4,5,8-tetracarboxylic bisimide of formula I:

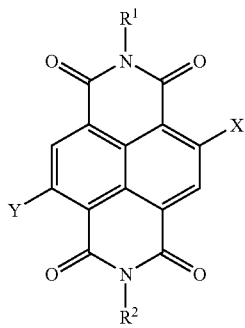

wherein:
X and Y are each independently selected from halogen or a radical of the formula NHR$^3$, wherein R$^3$ is C$_1$-C$_8$ branched or unbranched alkyl, and further wherein at least one of X and Y is other than halogen; and
R$^1$ and R$^2$ are each independently C$_1$-C$_{30}$ unbranched or branched alkyl or carboxyalkyl; or phenyl, wherein the phenyl is substituted one or more times by C$_1$-C$_8$ unbranched or branched alkyl.

2. The fluorescent naphthalene-1,4,5,8-tetracarboxylic bisimide of claim 1, wherein the C$_1$-C$_8$ branched or unbranched chain of NHR$^3$ terminates with a hydroxyl.

3. The fluorescent naphthalene-1,4,5,8-tetracarboxylic bisimide of claim 1, wherein R$^1$ and/or R$^2$ independently of one another are C$_1$-C$_8$ alkyl.

4. The fluorescent naphthalene-1,4,5,8-tetracarboxylic bisimide of claim 3, wherein the C$_1$-C$_8$ branched or unbranched alkyl is tert-butyl.

5. The fluorescent naphthalene-1,4,5,8-tetracarboxylic bisimide of claim 1, wherein R$^1$ and R$^2$ are each n-octyl.

6. The fluorescent naphthalene-1,4,5,8-tetracarboxylic bisimide of claim 1, wherein R$^1$ and R$^2$ are each 4-tert-butylphenyl.

7. The fluorescent naphthalene-1,4,5,8-tetracarboxylic bisimide of claim 1, wherein R$^1$ and R$^2$ are each 2-ethylhexyl.

8. The fluorescent naphthalene-1,4,5,8-tetracarboxylic bisimide of claim 1, wherein R$^1$ and R$^2$ are each a carboxyalkyl.

9. The fluorescent naphthalene-1,4,5,8-tetracarboxylic bisimide of claim 5, wherein:
X is chlorine; and
Y is n-octyl amino.

10. The fluorescent naphthalene-1,4,5,8-tetracarboxylic bisimide of claim 1, wherein:
X is chlorine; and
Y is n-octyl amino;
R$^1$ is 4-tert-butyl phenyl; and
R$^2$ is 4-tert-butyl phenyl.

11. The fluorescent naphthalene-1,4,5,8-tetracarboxylic bisimide of claim 5, wherein X and Y are each n-octyl-amino.

12. The fluorescent naphthalene-1,4,5,8-tetracarboxylic bisimide of claim 5, wherein X and Y are each 2-ethyl-hexyl amino.

13. The fluorescent naphthalene-1,4,5,8-tetracarboxylic bisimide of claim 12, wherein R$^1$ and R$^2$ are each 2-ethyl-hexyl.

14. A fluorescent naphthalene-1,4,5,8-tetracarboxylic bisimide of formula I:

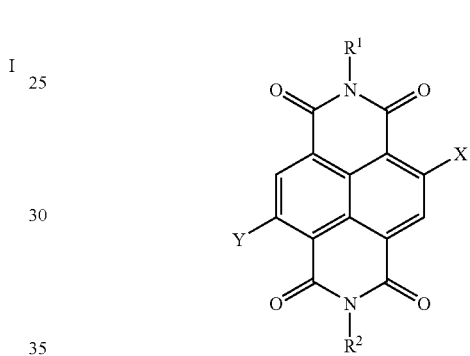

wherein:
X is butyl amino;
Y is chlorine;
R$^1$ is a carboxyalkyl; and
R$^2$ is a carboxyalkyl.

15. A fluorescent naphthalene-1,4,5,8-tetracarboxylic bisimide of formula I:

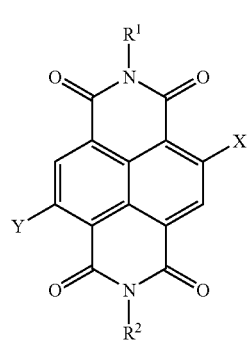

wherein:
X is 3-hydroxypropylamino;
Y is chlorine;
R$^1$ is a carboxyalkyl; and
R$^2$ is a carboxyalkyl.

* * * * *